(12) United States Patent
Nakamura

(10) Patent No.: US 7,655,218 B2
(45) Date of Patent: Feb. 2, 2010

(54) METHODS AND COMPOSITIONS FOR DETECTION AND DIAGNOSIS OF INFECTIOUS DISEASES

(75) Inventor: Reiko M. Nakamura, Musashino (JP)

(73) Assignee: Japan BCG Laboratory (JP)

( * ) Notice: Subject to any disclaimer, the term of this patent is extended or adjusted under 35 U.S.C. 154(b) by 271 days.

(21) Appl. No.: 11/020,974

(22) Filed: Dec. 22, 2004

(65) Prior Publication Data
US 2005/0106107 A1    May 19, 2005

Related U.S. Application Data

(60) Division of application No. 09/877,802, filed on Jun. 6, 2001, now Pat. No. 6,979,450, which is a continuation of application No. 09/244,701, filed on Feb. 4, 1999, now abandoned.

(60) Provisional application No. 60/073,911, filed on Feb. 6, 1998, provisional application No. 60/096,140, filed on Aug. 11, 1998.

(51) Int. Cl.
*A61B 8/00* (2006.01)

(52) U.S. Cl. .................. 424/9.81; 424/9.1; 424/9.2; 424/9.8; 424/248.1; 424/443; 424/810; 235/253.1; 235/287.2

(58) Field of Classification Search .......... 424/9.1, 424/9.2, 9.8, 78.02, 248.1, 443, 444, 445, 424/446, 447, 448, 810, 772, 9.81; 514/772; 436/63, 169; 435/30, 253.1, 286.1, 287.2, 435/63, 169
See application file for complete search history.

(56) References Cited

U.S. PATENT DOCUMENTS

| 4,965,192 A | | 10/1990 | Maes |
| 5,496,819 A | * | 3/1996 | Okuyama et al. ........ 514/226.5 |
| 5,709,879 A | | 1/1998 | Barchfeld et al. |
| 6,120,776 A | | 9/2000 | Haslov et al. |

FOREIGN PATENT DOCUMENTS

| EP | 0199362 A2 | 4/1986 |
| JP | 01-243997 | 9/1989 |
| JP | 06-169758 | 6/1994 |
| JP | 9206092 | 8/1997 |
| JP | 09206092 | * 8/1997 |
| JP | 09206092 | 12/1997 |
| WO | WO 95/01440 | 1/1995 |
| WO | WO 95/34328 A1 | 12/1995 |
| WO | WO 96/40236 | 12/1996 |

OTHER PUBLICATIONS

Haga, et al., Difference in Delay Skin Reaction to MPB64 Between BCG-Immunized and Tubercle Baccil-Infected Guinea Pigs, *Tubercle and Lung Disease*, vol. 75, Supplement 1, p. 54, 28th World Conference of IUATLD/UICTMR, Mainz, Germany, Jun. 14-17, 1994.
Haga, et al., Effective Isolation of MPB64 from a Large Volume of Culture Filtrate of *Mycobacterium bovis* BCG Tokyo, *JPN. J. Med. Sci. Biol.*, vol. 49, pp. 15-27 (1996).
Haga et al., Delayed Type Hypersensitivity to a recombinant mycobacterial antigen, MPB64, in guinea pigs sensitized to *Mycobacterium tuberculosis* or *Mycobacterium bovis* BCG, *Journal of Leukocyte Biology*, vol. 57, pp. 221-225 (1995).
Nakamura, et al., Tuberculosis Diagnosis with MPB64—Preliminary Study with a human being, "Kekkeku (Tuberculosis)", *The Japanese Society for Tuberculosis*, Feb. 15, 2996. Discusses results of preliminary studies conducted to test efficacy of MPB64 antigen administered to skin surface by way of hydrophilic ointment. Results were inconclusive and ointment was not defined.
Wilcke, et al., Clinical Evaluation of MPT-64 and MPT-59, two proteins secreted from *Mycobacterium tuberculosis*, for skin test reagents, *Tubercule and Lung Disease*, vol. 77, pp. 250-256 (1996).
Harboe et al., "Properties of Proteins MPB64, MPB70, and MPB80 of *Mycobacterium bovis* BCG", Infection and Immunity, vol. 52, No. 1, p. 293-302, 1986.
Nagai et al., "Specific Skin-Reactive Protein from Culture Filtrate of *Mycobacterium bovis* BCG", Infection and Immunity, vol. 31, No. 1, p. 1152-1160, 1981.
Wiker et al., "MPB59, a Widely Cross-Reacting Protein of *Mycobacterium bovis* BCG", Int. Archs Allergy appl. Immun., vol. 81, No. 4, p. 307-314, 1986.

* cited by examiner

*Primary Examiner*—Gailene R. Gabel
(74) *Attorney, Agent, or Firm*—King & Spalding

(57) ABSTRACT

Methods and compositions for the detection and diagnosis of infectious diseases are provided. In particular, efficient and sensitive methods and compositions for the detection of active mycobacterial disease are provided for distinguishing between individuals having active disease, and individuals who have been immunologically exposed, such as those infected with a mycobacterium but are without active disease, or those who have been vaccinated with BCG. The methods comprise topical application of antigen compositions for transdermal delivery.

6 Claims, 2 Drawing Sheets

METHODS AND COMPOSITIONS FOR DETECTION AND DIAGNOSIS OF INFECTIOUS DISEASES

CROSS REFERENCE TO RELATED APPLICATIONS

This application is a divisional of U.S. patent application Ser. No. 09/877,802 filed Jun. 6, 2001, now U.S. Pat. No. 6,979,450, which is a continuation of U.S. patent application Ser. No. 09/244,701, filed Feb. 4, 1999, now abandoned. U.S. patent application Ser. No. 09/244,701 claims priority to U.S. provisional application Ser. No. 60/073,911 filed Feb. 6, 1998 and to U.S. provisional application Ser. No. 60/096,140 filed Aug. 11, 1998.

FIELD OF INVENTION

The present invention relates to methods and compositions for detecting and diagnosing infectious diseases. In particular, the invention relates to transdermal delivery systems or devices comprising mycobacterial antigens, wherein the application of such systems or devices stimulates an immunological response sufficient for detection and diagnosis of active mycobacterial infection.

BACKGROUND OF THE INVENTION

The detection of infectious diseases is often accomplished by use of tests that monitor immunological responses. Many times, however such tests are cumbersome and frequently yield inconsistent results. In addition, the absence of sophisticated laboratory equipment often reduces the availability of testing to individuals living in underdeveloped areas where the occurrence of infectious disease may be disproportionately high. Accurate diagnosis and detection of infectious disease is important not only for treatment purposes, but also for the prevention of occurrence and dissemination of disease. The need for sensitive and accurate detection methods has become particularly pronounced recently especially in light of the increase in infections such as those caused by mycobacteria.

Mycobacterial infections often manifest as diseases such as tuberculosis. Human infections caused by mycobacteria have been widespread since ancient times, and tuberculosis remains a leading cause of death today. Although the incidence of the disease declined in parallel with advancing standards of living since at least the mid-nineteenth century, mycobacterial diseases still constitute a leading cause of morbidity and mortality in countries with limited medical resources and can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *M. tuberculosis* complex, commonly referred to as tuberculosis (TB), with approximately 8 million new cases and 3 million deaths attributable to TB yearly.

After decades of decline, TB is on the rise. In the United States, up to 10 million individuals are believed to be infected. Almost 28,000 new cases were reported in 1990, a 9.4 percent increase over 1989. A sixteen percent increase was observed from 1985 to 1990. Overcrowded living conditions and shared air spaces are especially conducive to the spread of TB, contributing to the increase in instances that have been observed in the U.S. in prison inmates and among the homeless in larger cities.

Approximately half of all patients with acquired immune deficiency syndrome (AIDS) will acquire a mycobacterial infection, with TB being an especially devastating complication. AIDS patients are at higher risks of developing clinical TB and anti-TB treatment seems to be less effective than in non-AIDS patients. Consequently, the infection often progresses to a fatal disseminated disease.

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue) and, consequently the prognosis for the infected AIDS patient is poor.

The World Health Organization (WHO) continues to encourage the battle against TB, recommending prevention initiatives such as the "Expanded Program on Immunization" (EPI), and therapeutic compliance initiatives such as "Directly Observed Treatment Short-Course" (DOTS). For the eradication of TB, diagnosis, treatment, and prevention are equally important. Rapid detection of active TB patients will lead to early treatment by which about 90% cure is expected. Therefore, early diagnosis is critical for the battle against TB. In addition, therapeutic compliance will ensure not only elimination of infection, but also reduction in the emergence of drug-resistance strains.

The emergence of drug-resistant *M. tuberculosis* is an extremely disturbing phenomenon. The rate of new TB cases proven resistant to at least one standard drug increased from 10 percent in the early 1980's to 23 percent in 1991. Compliance with therapeutic regimens, therefore, is also a crucial component in efforts to eliminate TB and prevent the emergence of drug-resistant strains.

Although over 37 species of mycobacteria have been identified, more than 95% of all human infections are caused by six species of mycobacteria: *M. tuberculosis, M. avium-intracellulare, M. kansasii, M. fortuitum, M. chelonae*, and *M. leprae*. The most prevalent mycobacterial disease in humans is tuberculosis (TB) which is caused by mycobacterial species comprising *M. tuberculosis, M. bovis*, or *M. africanum* (Merck Manual 1992). Infection is typically initiated by the inhalation of infectious particles which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology*, The C.V. Mosby Company 219-230 (1990)).

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. Avium. M. avium* bacilli occur in several distinct colony forms. Bacilli which grow as transparent or rough colonies on conventional laboratory media are able to multiply within macrophages in tissue culture, are virulent when injected into susceptible mice, and are resistant to antibiotics. Rough or transparent bacilli which are maintained on laboratory culture media often spontaneously assume an opaque colony morphology at which time they fail to grow in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both resistance to antibiotics and resistance to killing by macrophages have been attributed to the glycolipid barrier on the surface of *M. avium*.

Diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long a time as four to eight weeks. Species identification takes a further two weeks. There are several other techniques for detecting mycobacteria such as the polymerase chain reaction (PCR), *mycobacterium tuberculosis* direct test, or amplified *mycobacterium tuberculosis* direct test (MTD), and detection assays that utilize radioactive labels.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled. (See Murray et al. *Medical Microbiology*, The C.V. Mosby Company 219-230 (1990)).

Although tuberculin skin tests are widely used, they typically require 2-3 days to generate results, and many times, the results are inaccurate as false positives are sometimes seen in subjects who have been exposed to mycobacteria but are healthy. In addition, instances of mis-diagnosis are frequent since a positive result is not observed only in active TB patients, but also in BCG-vaccinated persons and those who had been infected with mycobacteria but have not developed the disease. It is hard therefore, to distinguish active TB patients from the others, such as household TB contacts, by the tuberculin skin test. Additionally, the tuberculin test often produces a cross-reaction in those individuals who were infected with mycobacteria other than *M. tuberculosis* (MOTT). Diagnosis using the skin tests currently available is frequently subject to error and inaccuracies.

What is needed are effective tests for detecting the presence of mycobacterial infection. In particular a test that does not require the invasion of the skin surface of the tested person would minimize the exposure of the health care professional administering the test to the bodily fluids of the tested person and lessen the risk of transmission of other infectious agents that may be present in the tested person. In addition, a test that is easily administered and has an easily determined positive or negative outcome is essential when monitoring compliance with a therapeutic regimen for highly infectious diseases such as tuberculosis, particularly in individuals such as homeless persons, prison inmates, schoolchildren and senior citizens.

What is also needed are inexpensive and accurate methods for distinguishing between persons who have active disease states and those persons who have only been immunologically exposed to infectious agents, (such as those persons previously infected with a mycobacterium) but are without active disease, or those persons who have been vaccinated with BCG. Additionally, there is no known method for monitoring the effects of drug therapy in persons infected with a mycobacterium, such as tests that can distinguish between active tuberculosis and other stages of healing or prior exposure. Furthermore, what is also needed is a test that can be easily administered to children, who are especially afraid of currently used skin tests that involve needles or puncturing the skin. Such tests are particularly desirable for monitoring patients particularly AIDS patients who are highly susceptible to mycobacterial infection. In addition, tests that are easily administered and have an easily determined positive or negative outcome are essential when monitoring a disease such as tuberculosis in homeless persons or prison inmates.

SUMMARY OF THE INVENTION

The present invention comprises methods and compositions for the detection of infectious diseases. In accordance with a preferred embodiment of the present invention, transdermal delivery systems or devices, such as patches containing mycobacterial antigen compositions, are provided. Such patches are worn on the skin and removed after a predetermined amount of time. The skin is then examined for an immunogenic response to the presence of the antigen in the patch.

Unlike prior art methods, the diagnostic methods and compositions provided herein are highly sensitive and specific. Most importantly, the diagnostic methods and compositions of the present invention are especially effective in detecting *M. tuberculosis* infection in active tuberculosis patients thereby eliminating the possibility of misdiagnosing individuals who have received vaccines or have been otherwise exposed to the organism without disease manifestation.

The diagnostic methods described herein include the topical application of compositions comprising mycobacterial antigens including, but not limited to, MPB44, MPB45, MPB51, MPB59, MPB64, MPB70, MPB80 or MPB83, for transdermal delivery to skin and for subsequent detection of an immunogenic response. The antigens may be applied individually or in combination. Particularly preferred is the topical application of an antigen composition comprising MPB64. The present invention contemplates any antigen that has the characteristics of MPB64, in that there is a delayed-type hypersensitivity reaction to the antigen in the presence of active tuberculosis disease, and no reaction where there has been no exposure to mycobacteria, or in exposure via vaccine or other non-active tuberculosis state.

Accordingly, it is an object of the present invention to provide methods and compositions for the detection of infectious diseases.

Another object of the present invention to provide methods and compositions for the detection of active tuberculosis.

It is another object of the present invention to provide methods and compositions for the detection of active tuberculosis using topical application of antigen compositions for transdermal delivery to the skin.

Another object of the present invention to provide methods and compositions for the detection of mycobacterial infections.

Yet another object of the present invention to provide methods and compositions for the detection of active disease caused by mycobacterial species comprising *M. tuberculosis* complex, *M. avium-intracellulare, M. kansasii, M. fortuitum, M. chelonae, M. leprae, M. africanum*, and *M. microti*.

Another object of the present invention to provide methods and compositions for the detection of active disease caused by *M. tuberculosis*.

It is yet another object of the present invention to provide methods and compositions for the detection of active disease caused by *M. bovis*.

Another object of the present invention is to provide methods and compositions for the immunological detection of mycobacterial infection, that utilize topical application without requiring invasive procedures.

Yet another object of the present invention is to provide sensitive diagnostic methods and compositions for the detection of active disease caused by mycobacteria wherein antigen compositions are topically applied and transdermally delivered and skin is subsequently examined for an immunogenic response.

Another object of the present invention is to provide methods and compositions for the detection of active disease caused by mycobacteria wherein the topically applied mycobacterial antigen composition comprises MPB44, MPB45, MPB51, MPB59, MPB64, MPB70, MPB80 or MPB83.

Yet another object of the present invention is to provide methods and compositions for the detection of active disease caused by mycobacteria wherein the topically applied mycobacterial antigen composition comprises MPB44, MPB45, MPB51, MPB59, MPB64, MPB70, MPB80 or MPB83, wherein the antigen is applied either individually or in combination with another mycobacterial antigen.

It is another object of the present invention to provide methods and compositions for the detection of active disease caused by mycobacteria wherein the topically applied mycobacterial antigen composition comprises MPB64.

Yet another object of the present invention is to provide methods and compositions for diagnosis of infectious disease that is easy to administer.

An additional object of the invention is to provide methods and compositions for detection of active tuberculosis for monitoring the effectiveness of therapeutic treatments.

Another object of the present invention is to provide a kit for diagnosis and detection of active disease caused by mycobacteria.

Yet another object of the present invention is to provide methods and compositions for detection of active disease caused by mycobacteria in household TB or mycobacterial disease contacts.

It is another object of the present invention to provide methods and compositions for the monitoring of the clinical status of a mycobacteria-infected patient following chemotherapy.

Another object of the present invention is to provide sensitive diagnostic methods and compositions for children with active tuberculosis.

It is a further object of the present invention to provide sensitive methods and compositions for the detection of active disease caused by mycobacteria wherein the method involves the use of a skin patch.

These and other objects, features and advantages of the present invention will become apparent after a review of the following detailed description of the disclosed embodiments and the appended claims.

DETAILED DESCRIPTION

Figure 1:
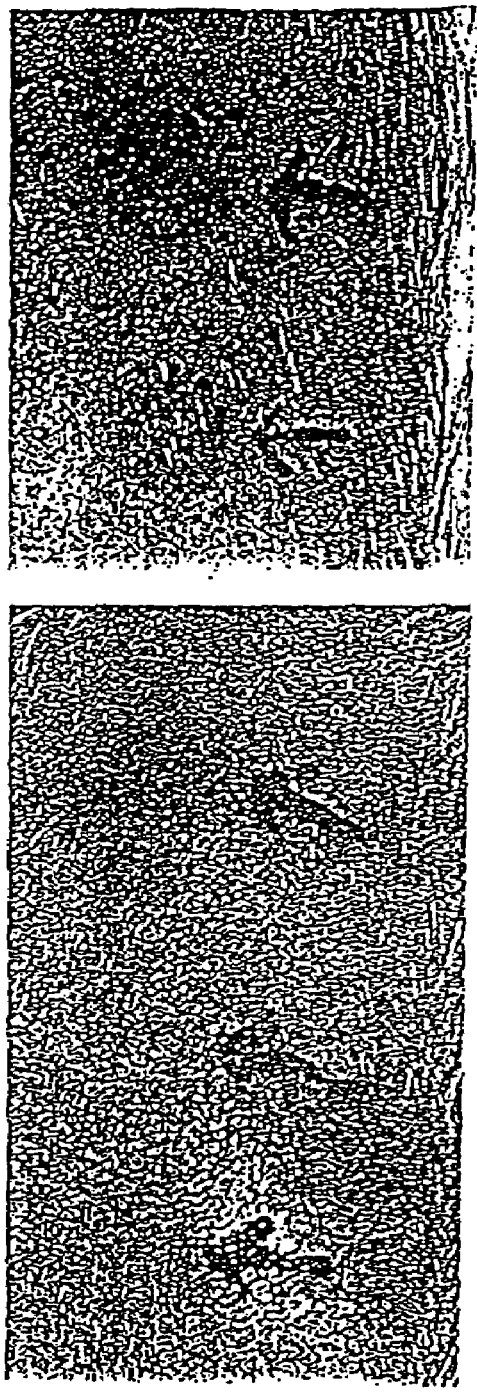
FIG. 1 shows photographs of the dose response of varying amounts of MPB64 antigen by skin reactions in guinea pigs.

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference, including U.S. provisional application Ser. No. 60/073,911 filed Feb. 6, 1998, and U.S. provisional application Ser. No. 60/096,140 filed Aug. 11, 1998.

Mycobacterial infections such as those causing tuberculosis, once thought to be declining in occurrence, have rebounded and again constitute a serious health threat. Areas where humans are crowded together or living in substandard housing are increasingly found to have persons infected with mycobacteria. Persons who are immunocompromised are at great risk of being infected with mycobacteria and dying from such infection. In addition, the emergence of drug-resistant strains of mycobacteria has added to the treatment problems of such infected persons.

Many people who are infected with mycobacteria are poor or live in areas with inadequate health care facilities. Such people are not easily tested for mycobacterial infection and need inexpensive and noninvasive methods for detection of infections. Additionally, persons who are in prison or are homeless, generally have inadequate healthcare, poor physical condition and adequate or successful health care intervention is typically unavailable.

The present invention provides methods and compositions comprising topical applications of antigen compositions for transdermal delivery of antigens, particularly mycobacterial antigens. More particularly, the present invention provides methods and compositions for detecting disease such active tuberculosis, and distinguishing persons with active disease from persons who have only been exposed immunologically to infectious agents such as mycobacteria.

The methods and compositions of the present invention may be used for testing the presence of mycobacteria infection in humans as well as other animals. For example, the present invention may be particularly useful for the detection of disease in cows infected with *M. bovis*.

Medically "active tuberculosis" is diagnosed by the well known medical procedures of chest X-ray (CXR), sputum tests, or other symptoms. Because precise identification of the presence of mycobacterial infectious agents is expensive and takes a long time, diagnosis of active disease does not necessarily include the identification of the presence of mycobacteria. Accordingly, diagnosis of active disease such as tuberculosis may be dependent upon detecting other aspects of mycobacterial infection such as the generation of particular immune responses or the manifestation of certain symptoms.

As used herein the term "tuberculosis" comprises disease states usually associated with infections caused by mycobacteria species comprising *M. tuberculosis* complex. Mycobacterial infections caused by mycobacteria other than *M. tuberculosis* (MOTT) are usually caused by mycobacterial species comprising *M. avium-intracellulare, M. kansasii, M. fortuitum, M. chelonae, M. leprae, M. africanum*, and *M. microti*.

The present invention includes methods and compositions for topical application enabling transdermal delivery of antigens that elicit an immune response, such as a delayed-type hypersensitivity response in persons who have active disease such as tuberculosis caused by mycobacterial infections. Such antigens are derived from mycobacteria, or are cross-reactive with mycobacterial proteins or carbohydrate moieties. Preferred antigens comprise those that are derived from mycobacteria including, but not limited to, MPB44, MPB45, MPB51, MPB59, MPB64, MPB70, MPB80 or MPB83. A particularly preferred is antigen MPB64. (see Kawajiri et al. Japanese Patent Application, Pub. No. 09206092 which is incorporated by reference herein in its entirety).

Another preferred combination of antigens comprises the combined use of MPB64 and MPB59. For example, combination of MPB59 and MPB64 may indicate the infection of atypical mycobacteria since a subject infected by other kinds of mycobacteria that do not secrete MPB64 will show a positive response to MPB59.

MPB64 is a mycobacterial antigen frequently associated with the *M. tuberculosis* complex. It was first described as MPT64 by Harboe et al. (Infect. Immun. 1986; 52:293-902, which is herein incorporated in its entirety), and has been well characterized and used in various laboratories since then. (See for example Yamaguchi et al. Infect. and Immu. 1989; 57:283-288, which is also incorporated herein in its entirety.) "MPB64" and "MPT64" refer to the same antigen: MPT64 was isolated from the culture filtrate of *M. tuberculosis*, and was therefore named as mycobacterial protein of tuberculosis, and MPB64 was later isolated from the culture filtrate of *M. bovis* (or BCG) and was therefore named as mycobacterial protein of *bovis*. It was subsequently discovered that both proteins are the same. MPB64 and MPT64 refer to antigens secreted from mycobacteria species including, but not limited to, *M. tuberculosis, M. bovis*, and some strains of *M. bovis* BCG. The antigen is secreted during bacterial growth and is immunogenic, eliciting delayed-type hypersensitivity (DTH) in guinea pigs and humans.

Recombinant antigens may also be used in the diagnostic methods and compositions contemplated by the present invention. See for example Haga et al., Journ. of Leukocyte Biology 1995; 57:221-225; Roche et al., Clin. Exp. Immunol. 1996; 103(2)226-232; and Roche et al., J. Infect. Dis. 1994; 107(5):1326-30, each of which is incorporated herein in its entirety.

The antigens of the present invention are topically applied for transdermal delivery into the skin of the person to be tested. The antigen is applied by maintaining a composition comprising the antigen in close contact with the skin. The concentration of the antigen in the composition is in a range of approximately 1 to 150 micrograms/dosage applied, most particularly 30 to 75 micrograms/dosage applied. The antigen composition may comprise a physiologically effective solution comprising surfactants, buffers and solvents that enable transdermal delivery of the antigen composition. Preferably surfactants, buffers and solvents that improve permeation and transport of the antigen, and that do not themselves trigger a reaction or interfere with the immunogenicity of the antigen, are used. Preferred surfactants for the antigen composition comprise TWEEN®, TWEEN® (polysorbate surfactant) 40, TWEEN® 60, and TWEEN® 80; each of which may be used at concentrations ranging from 0.001-10%, 0.001-1% and preferably 0.005%, in phosphorous saline. A preferred embodiment for the application comprises 30 to 75 micrograms of antigen in 100 microliters of phosphate buffered saline further comprising the preferred surfactant TWEEN® 80. A most preferred embodiment for application is 75 micrograms of antigen in 100 microliters of phosphate buffered saline (PBS) with 0.005% TWEEN® 80. Prepared antigen compositions may be stored in suitable aseptic glass or plastic containers, in batches or aliquotted according to desired quantities The present invention is particularly directed to methods of transdermal delivery of antigen compositions to skin cells for the detection of active disease. Accordingly, all contemplated solvent and antigen combinations that enable the delivery of infectious agent antigens to skin cells, and result in the detection of active disease, are included herewith.

As used herein, the term "transdermal delivery" refers to the delivery of a composition to all layers of the skin, including but not limited to, the epidermis (stratum corneum, stratum lucidum, stratum granulosum, stratum spinosum, stratum basale), the dermis, and the subcutaneous layer. As used herein, the term "topical application" refers to the application or placement of a composition on skin without puncturing or otherwise invasively entering the skin by use of needles and the like.

A preferred embodiment of the present invention comprises a transdermal delivery system or device for holding the compositions described above in close contact with the skin of a person. A highly preferred embodiment comprises a patch band, such as a skin patch band, for holding the composition in close contact with the skin. Materials that are suitable for use in the patch for delivering the antigen composition of the present invention include TORII's patch band TORIIBAN™ (obtained from Torii and Co., Ltd, Tokyo), FINN-CHAMBER®, and Perme-aid S. (Nitto-Denkou Co. Japan). In addition, materials such as medical adhesive plaster or tape includes a portion of a material impregnated with the antigen composition, and wherein the material is located so that it is in direct contact with the skin. Suitable medical adhesive plasters, tapes and fabrics are made by numerous manufacturers such as Nichiban (Japan), Kimberly-Clark (Neenah, Wis.) and 3M (St. Paul, Minn.). The device may be held in place by various fastening means well known to those skilled in the art. For example, the device may be tied to the subject's arm by use of a string, or it may be attached by an adhesive. Preferably, material such as the adhesive used for holding the device in place should be gas permeable and water-resistant so that it does not fall off as a result of becoming wet due to perspiration or bathing.

One particularly advantageous aspect of the present invention relates to the ease with which the invention may be used and executed. For example, integrity of the antigen compositions may be preserved by shipping or maintaining compositions in aseptic containers under appropriate temperature conditions. The antigen compositions may be stored in aliquots of desired amounts, for example, 100 or 200 μl, and then applied to gauze, plaster or tape or the like, as necessary for testing patients. Furthermore, each of the components necessary for the compositions and methods of the present invention may be provided together in a kit to facilitate use.

In addition to a patch-type embodiment, the present invention may also take the form of other transdermal drug delivery vehicles known to those skilled in the art, including, but not limited to, gels, creams, liquid sprays and the like.

A preferred method contemplated by the present invention comprises the topical administration of a composition comprising mycobacterial antigen for transdermal delivery to the skin of a human. For example, a patch containing the antigen composition is applied to the forearm of a person and held in close contact with the skin. The patch is left in place for a predetermined amount of time so as to enable sufficient transdermal administration of the antigen. Such an amount of time may range from 1 to 7 days, preferably 2 to 5 days, most preferably 3 days. After the specified time has passed, the patch is removed and the skin is examined for an immunogenic response.

It is known in the art that a delayed-type hypersensitivity reaction is observed in skin in response to the presence of some antigens. Typically such reactions are observed following invasive introduction of an antigen composition, and usually such reactions are characterized by redness, erythema, induration (raised thickening of the skin), presence of red vesicles or ulcers. The response looked for in the present method is similar to the response seen with the intradermal injection of mycobacterial antigen.

The inventors of the present invention have surprisingly found that transdermal delivery by topical application the antigens of the present invention, cause an immunogenic response (specifically a delayed-type hypersensitivity (DTH) reaction) in persons who have active mycobacterial disease such as tuberculosis. As shown in the examples herein, TB-infected guinea pigs express a delayed-type hypersensitivity skin reaction to the antigen MPB64 as long as the bacteria continue to grow, in contrast guinea pigs immunized with BCG-Tokyo lost delayed-type hypersensitivity to MPB64 some time after vaccination. As discovered by the inventors, the methods and compositions of present invention, comprising mycobacterial antigens, particularly MPB64, can be used for the diagnosis of active mycobacterial disease such as active TB. Suprisingly, individuals who were infected with *M. tuberculosis* but had not developed tuberculosis, and individuals who had previously received BCG vaccinations, do not show a positive skin reaction in response to MPB64.

The novel discovery of transdermal delivery of antigens by topical application, particularly MPB64, for diagnosing active mycobacteria disease such as tuberculosis, is especially desirable because no invasive procedures are required. In fact, intradermal delivery of MPB64 has been recently shown to be unsuccessful for distinguishing between TB patients and healthy controls (Wilcke et al. Tubercle and Lung Disease (1996) 77:250-256). Effective transdermal delivery of mycobacterial antigens by topical application was heretofore unknown, and using the methods and compositions of the present invention, the inventors have successfully developed diagnostic procedures for distinguishing between active TB patients and healthy PPD-positive controls.

Although not wishing to be bound by the following theory, it is thought that one reason intradermal injection of antigen may be less effective than transdermal application is related to solubility aspects of the antigen and/or inadequate opportunity for antigen presentation. For example, it is possible that with intradermal injection the antigen is quickly dissolved in body fluids with insufficient time for the immune system to recognize and/or respond to it. In contrast, the novel methods of the present invention enable the antigen to be gradually introduced to the subject's immune system, and as the antigen slowly permeates through the skin pores and sweat glands into the intradermal local portion, there is enough time for the immune system to mount a response, typically in the form of a delayed-hypersensitivity reaction. It is also possible that intradermal and transdermal introduction of antigen elicit distinct immune responses.

Although not wishing to be bound by the following theory, it is thought that hypersensitivity reactions (also known as Type IV or cell mediated immunity reactions) are mediated largely by T cells with consequent involvement of monocytes. Such reactions typically have responses that are observed after a passage of time, i.e. 18-24 hours, and are therefore referred to as delayed-type hypersensitivity. It is thought that an antigen presenting cell presents the antigen to a T cell and following activation, the T cells release lymphokines that cause accumulation and activation of macrophages, monocytes and nonimmune lymphocytes.

The present invention may also be used to detect active tuberculosis in household contacts of previously infected TB patients. This allows for the monitoring of the spread of the disease to others in close contact with the originally infected persons. Because members of the public may have tuberculosis and spread it by coughing, the present invention can be used to monitor the exposure of persons who work with the public, such as airline stewards or health care professionals. Persons who work with the homeless or prison populations are also easily monitored for the presence of active tuberculosis.

An especially desirable use of the present invention is the monitoring of the effectiveness of treatment of persons with mycobacterial infections. For example, the ability to detect when the active tuberculosis patient no longer has active TB, thus, the treatment is effective, is highly desirable with the rise in drug-resistant mycobacteria. A preferred method includes topically applying the antigens of the present invention to the person with active TB prior to treatment, and after a sufficient time, observing the skin reaction. At a later point in the treatment regimen, the antigens are again applied and the skin reaction is observed. Lack of response by the skin indicates that the treatment has been effective in changing the active tuberculosis state. A continued response by the skin indicates that the treatment either is not effective, or that there has not been enough time for the treatment to be effective, and the person still has active TB. At this time, the treatment could be changed, the drug sensitivity of the infecting mycobacterium could be determined, or the same treatment could be continued for a longer amount of time.

One use of the present invention would be for rapid screening of a population such as when investigating a neighborhood or slum for infection rates, for testing incoming prisoners, or a group of homeless persons in a shelter or on the street. For example, incoming prisoners would have patches containing the antigens of the present invention issued to them upon entry to the prison. After the specified time of wearing the patch, the skin reactions of the prisoners are examined. Those with positive reactions would be housed separately. Because the present invention detects active TB, those prisoners could be isolated from the other prisoners and immediately begin treatment. Other tests for TB would enable detection of prisoners who have had exposure to TB at some time in their lives, and who may not be capable of transmitting TB to others. There is no need to isolate and treat persons who are not capable of transmitting TB to others.

In many parts of the world, persons are vaccinated against TB. It is extremely difficult to detect active TB in these persons because with standard TB skin tests, all persons exposed to mycobacteria test positive, whether there is active TB or the effects from vaccination. The present invention is used in such areas to detect the presence of active TB in individuals and distinguish such individuals from those who were previously vaccinated.

The ease of administration is a particularly beneficial aspect of the present invention. For example, children are not frightened by the application of a topical device, such as a patch, and are not hesitant to wear such a device for a time sufficient to create a skin response. Such topical devices as patches are easily stored and transported to isolated places that may lack refrigeration and clean water. The present invention can be made from inexpensive materials that can be produced at low cost and used by health care organizations worldwide.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

To test the development of a new, simple and rapid diagnostic method for active tuberculosis, subjects were tested for skin reaction to the antigen MPB64 by a transdermal delivery method following topical application of an antigen composition using removable patches.

Skin Patch Preparation

Although antigens such as MPB59, MPB70, MPB44, MPB45 or MPB51 or MPB64 may be used in the patch test of the present invention, in the following example the antigen used was MPB64 in a concentration of approximately 75 μg per patch. It is contemplated that approximately 50 to 100 μg of antigen may successfully be used per patch. A preferred antigen solution comprises approximately 750 μg antigen per ml of phosphate buffered solution (PBS), wherein the PBS consists of 0.005% TWEEN 80.

The patches were applied on the skin of the test subjects, left on for three days, and the results were interpreted by observing the site following removal of the patch. The presence of an immunological response such as a delayed-type hypersensitivity (DTH) reaction (redness, induration, or small red vesicles indicated a positive result), i.e. the presence of active tuberculosis. No change at the site was concluded as a negative response.

Test Subjects 53 patients with active tuberculosis, and 43 healthy purified protein derivative (PPD) positive controls were tested to determine whether or not the reaction to MPB64 was positive only in active tuberculosis patients. Tuberculosis patients from four clinics, in the vicinity of Manila, Philippines, Our Lady of Grace Parish, Sto. Nino de Tondo Parish, Canossa Health and Social Center, and Health Care Development Center, were examined.

Of the 53 active tuberculosis patients, 52 showed positive reaction to MPB64, while none of the 43 PPD-positive controls had a positive reaction to MPB64. The specificity of MPB64 for active tuberculosis was 100% and the sensitivity was 98.1%. Efficacy of the test was 98.9%.

The patch test with MPB64 is an effective and accurate method for the diagnosis of active tuberculosis, distinguishing such patients from BCG-vaccinated individuals and those naturally infected, but not developing tuberculosis. The experimental design for this finding is more fully described in Example 2.

EXAMPLE 2

To determine the reliability of MPB64 as a specific antigen for diagnosing active TB using the skin patch method, comparative tests were conducted among three different classes of individuals:

(1) active TB patients (2) healthy tuberculin-positive persons (3) household TB-contacts Correlation between skin reaction to MPB64 and the clinical status of TB in humans was observed. Because the purpose of this study was to determine the reliability of MPB64 as the specific diagnosing antigen for active TB, the selection of active TB patients was most important.

Clinical records of the outpatients coming to the clinics were checked. Those patients who were sputum-smear positive, had an abnormal CXR, and had clinical symptoms indicating active TB were classified as active TB patients, Group 1. Culture results were not available in most cases. The patients who had started chemotherapy shortly before were preferable because the effect of long-term chemotherapy on the MPB64 skin reaction was not known. However, there were some patients in Group 1 who had been treated for 6 months. They were considered as active TB patients because of positive smears in recent examinations and because of their symptoms.

The patients were living near the clinics where the socio-economic conditions were very poor. The geographical situation of their residences was important because they were scheduled to return to the clinic 3 days later for the results to be read. Only 12 out of 105 patients tested did not return. Among the patients who returned, 53 were available for the final analysis. The analysis is shown in Example 1. The rest of the subjects were excluded because their patches had been removed or fallen off before the reading day.

The patients were screened according to their clinical records and only those who were smear positive, had an abnormal CXR and had other symptoms such as cough, fever, or weight loss to indicate TB were selected as active TB patients. Culture positive patients were preferable, but the results of culture were available in only seven cases. Most of the active TB patients had been on chemotherapy for 1-4 months. Some had been treated for 6 months at the time of the study. Healthy tuberculin-positive volunteers were Filipinos and Japanese who did not show any sign of TB. At the time of the test, some family members came to the clinic along with TB patients. They were tested as “household TB-contacts”. All the subjects were informed of the outline of the study and gave consent for the test. The number of subjects in the three groups were as follows; Group 1, active TB patients, 53; Group 2, healthy controls, 43; and Group 3, household TB-contacts, 41.

MPB64 was isolated from an 8-day culture filtrate of *M. bovis* BCG Tokyo (obtained from Japan BCG Laboratory, Tokyo, Japan). The purified protein was suspended in PBS and stored at −20° C. The amount of protein was measured by Lowry’s method. Ammonium sulfate-precipitated whole protein from the 8-day culture filtrate of *M. bovis* BCG was named PPD-eT to distinguish it from purified protein derivative tuberculin (PPD), and used as the control for the patch test. PPDs prepared from *M. tuberculosis* Aoyama B was obtained from Japan BCG Laboratory (Tokyo, Japan). Five tuberculin units (TU) of PPDs suspended in 0.1 ml of reconstitution buffer were used for the Mantoux test with an intradermal injection.

Materials for the Patch Test

TORII's patch band TORIIBAN™ (obtained from Torri and Co., Ltd., Tokyo) of 15-mm gauze size was used. The antigen solution (75 μg of the antigen in 100 μl of PBS containing 0.005% TWEEN® 80) was applied on the gauze and the patch was attached to a forearm of a human subject after cleaning with alcohol the skin area to which the patch is applied. The patch was placed on the subject's skin such that the gauze was impregnated with the antigen solution contacted with the skin directly. The patch was left on for 72 hours.

Patch Test Schedule

Active TB patients and tuberculin-positive healthy controls were tested for a skin reaction to the MPB64 patch on the left arm, and to the PPD-eT patch on the right arm. Each patch contained 75 μg of antigen. A PPD (5 TU/100 μl) dose was injected intradermally into the right forearm in a place separate from the patch. A PPD-eT patch was used to confirm that the protein antigens did get into the body transdermally. If the PPD test was positive and the PPD-eT patch test was negative, transdermal administration was incomplete. Such cases were excluded from the test results.

The attached patch was removed 3 days later (72 hr) and the reaction was read as positive or negative. No change in the skin at the site was "negative", while erythema, induration, or a few small red vesicles at the site were recorded as a "positive" response to the antigen.

We have compared applying the patch on the forearm and the upper arm. Patches detached more easily from the upper arm (41.2%) than the forearm (17.6%) before the reading day. Therefore, the forearm is recommended for the test in adults.

Statistics

The two-by-two contingency test was used to evaluate the results of the MPB64 patch tests in humans.

Active TB Patients and Tuberculin Positive Healthy Controls

Table 1 shows the actual numbers in Groups 1 and 2 with positive or negative reaction to MPB64. All the subjects were positive to the PPDs Mantoux test and the PPD-eT patch test. From these results, the following values were calculated: Sensitivity, 98.1%; Specificity, 100%; False positive rate, 0%; False negative rate, 1.9%: Positive predictive value, 100%; Negative predictive value, 97.7%; Efficacy of the test, 98.9%. The results indicated that the MPB64 patch test is an effective method to distinguish active TB from healthy tuberculin-positive persons.

TABLE 1

MPB64 Patch Test
Two-by-Two Contingency Test Between Group 1 and Group 2

| Group | Positive | Negative | Total |
| --- | --- | --- | --- |
| 1: TB Patients | 52 | 1 | 53 |
| 2: Healthy Controls | 0 | 43 | 43 |
| Total | 52 | 44 | 96 |

Household TB-Contacts

The number of household TB-contacts (Group 3) were 41 including 12 males and 29 females. The results of the patch test are shown in Table 2. There were 26 subjects showing a positive reaction to both PPD-eT and MPB64 patches (63.4%), and nine subjects positive to PPD-eT but negative to MPB64 (22.0%). Six persons (14.6%) were negative to PPD-eT and MPB64. Among these double-negative persons, three were negative in PPDs Mantoux test.

The subjects in Group 3 were not registered as TB-patients at the clinic. The clinical status of each person was not known although some symptoms suggesting TB were observed.

TABLE 2

Patch Test with MPB64 and PPD-eT in Household TB-contacts

| | PDD-et/MPB64 | | | |
| --- | --- | --- | --- | --- |
| Subjects | +/+ | +/− | −/− | Total |
| Male | 7 | 3 | 2 | 12 |
| Female | 19 | 6 | 4 | 29 |
| Total | 26 | 9 | 6 | 41 |

From this study it is strongly suggested that MPB64 patch test is a promising tool for rapid diagnosis of active TB. It can distinguish active TB patients from individuals who were vaccinated with BCG or those who were TB-infected but had not developed the disease with 98.1% sensitivity and 100% specificity. The patch test also has advantages over an intradermal injection in the technical ease and the safety of its application. Though no wishing to be bound by any theory, it is thought that the patch test can supply antigen continuously for response by the patient.

EXAMPLE 3

In order to determine the reliability of MPB64 as a specific diagnosing antigen for active TB using the skin patch method, comparative tests were conducted on guinea pigs.

Female albino Hartley guinea pigs weighing 300 to 400 g at the beginning of the experiments, were purchased from Japan Laboratory Animals, Inc., Tokyo. Animals were maintained under specific pathogen free conditions at the Japan BCG Laboratory.

Antigens

Antigens were prepared according to the methods and materials set forth in Example 2.

Immunization of Guinea Pigs

Live BCG vaccine (Japan BCG Laboratory, Tokyo, Japan) was reconstituted according to the manufacturer's instructions and injected subcutaneously without adjuvant into guinea pigs at a dose of 0.5 mg per animal. The animals were tested between 4 and 25 weeks after the BCG injection.

Materials of Patch Test

TORII's patch band (Torri and Co., Ltd. Tokyo, Japan) of 7-mm gauze size was used. An antigen solution (75 μg of antigen in 15 μl of PBS containing 0.005% TWEEN® 80) was applied on the gauze, and the patch was attached to a shaved area of each guinea pig.

MPB64 was applied to a patch at various doses as indicated in FIG. 1 and the patches were attached to the right and left flanks of a BCG-immunized guinea pig, where the hairs had been removed.

Patch Test Schedule

Patches were removed at 24 hours and the reaction was read immediately. No change in the skin at the site was "negative", while erythema, induration, or a few small red vesicles at the site were recorded as a "positive" response to the antigen.

Dose Response to MPB64 in the Patch Test in BCG-Immunized Guinea Pigs

Guinea pigs immunized with BCG Tokyo 4 weeks previously were used for the MPB64 patch test with various doses of the antigen. The highest dose for the patch test was 75 μg/patch. The animals were tested with the patches containing MPB64 in various doses between 2.3 and 7.5 μg/patch. The patches were removed 24 hours later and the reaction was read as positive or negative. To make sure the animals were sensitized to BCG, 0.05 μg of the PPDs in 0.1 ml of the buffer was injected intradermally and the skin reaction was measured at 24 hours. FIG. 1 shows the results of the dose-response experiment. The response to MPB64 was positive at a dose of 4.7 μg/patch or higher concentration. Positive reaction was not observed at a dose of 2.3 μg of MPB64 per patch. Negative control patches which contained only PBS containing 0.005% TWEEN® 80 did not elicit any skin reaction in the BCG-immunized guinea pigs. Non-immunized guinea pigs did not show any response to either PPDs nor MPB64.

Time Course of the Skin Reaction to MPB64 in BCG-Immunized Guinea Pigs

Figure 2:
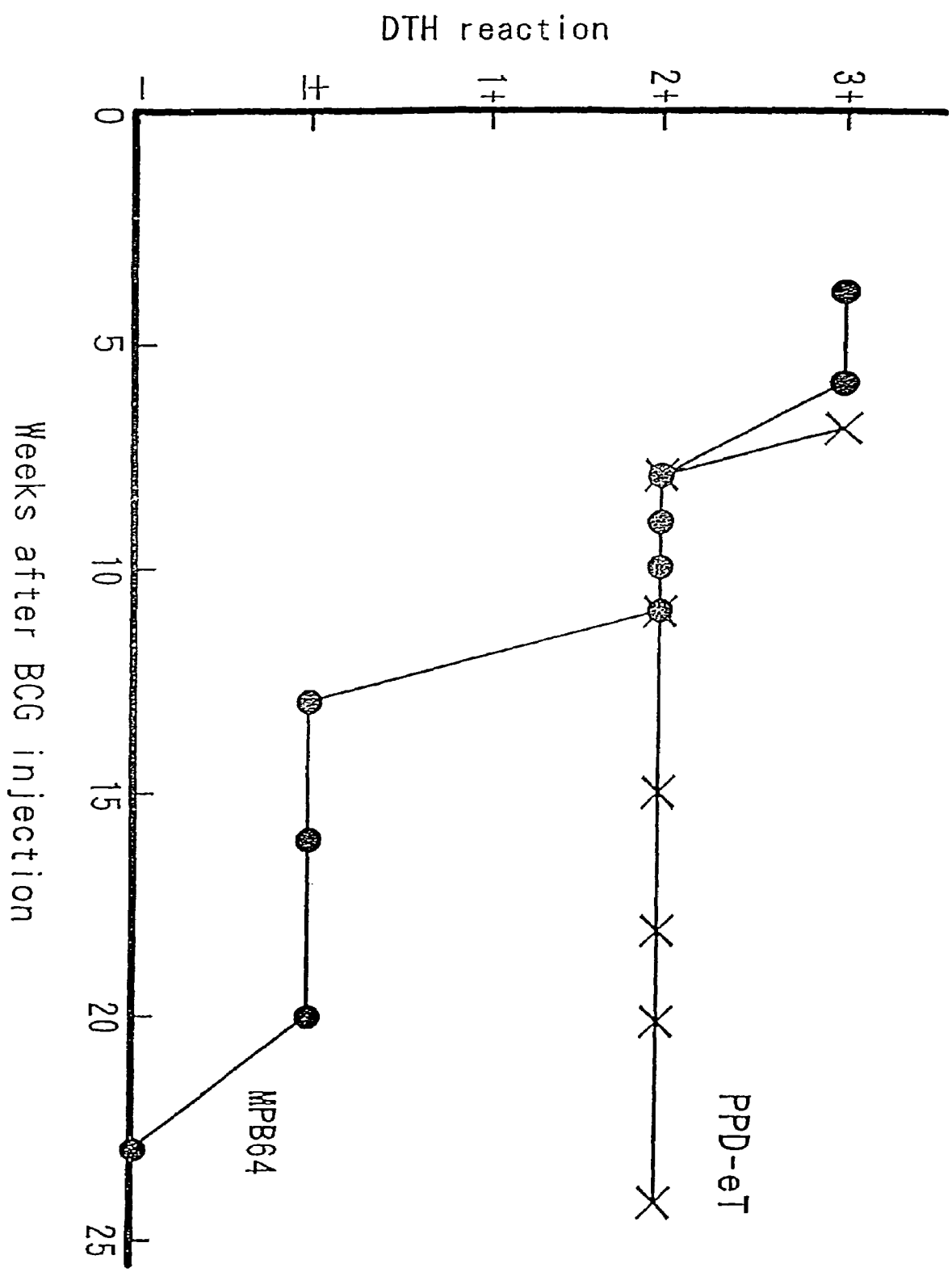
FIG. 2 is a graph showing the time course of delayed-type hypersensitivity response to a patch with MPB64 antigen following inoculation of guinea pigs with BCG.

It is known that BCG-immunized guinea pigs lost skin reaction to MPB64 15 weeks after BCG immunization when tested by the intradermal injection of MPB64. To address the question of whether this was true in the case of the patch test, guinea pigs were immunized with BCG Tokyo and tested with MPB64 patches at various times after the BCG injection. Individual animals were tested only one time to avoid the booster effect. As the control, a PPD-eT patch test was applied at the same time to each animal. The results are shown in FIG. 2. DTH was expressed as 3+, 2+, etc., because the diameter of a reaction was regulated by the size of a patch, not by the antigen dose. The skin reaction to the MPB64 patch test was positive in all the animals until 13 weeks after the BCG injection. It became hardly detectable afterwards, and was completely negative at 23 weeks. In contrast, the reaction to the PPD-eT patch test remained positive until the end of the experiment at 25 weeks after BCG injection.

Delayed-type hypersensitivity (DTH) to MPB64 and PPD-eT were examined at various times after the BCG injection. Each point of FIG. 2 represents the delay-type hypersensitivity of 3 guinea pigs expressed as follows: 3+, erythema and induration; 2+, erythema; 1+, small vesicles; +/−, faint colored (questionable reaction); −, no reaction.

Patch tests in guinea pigs confirmed that 1/16 of the antigen dose used for humans elicited a positive reaction.

It should be understood, of course, that the foregoing relates only to preferred embodiments of the present invention and that numerous modifications or alterations may be made therein without departing from the spirit and the scope of the invention.

We claim:

1. A method of distinguishing a patient with an active tuberculosis infection from a patient that has been exposed to a *Mycobacterium tuberculosis* but does not have active disease, or from a patient that has been previously vaccinated against *Mycobacterium tuberculosis* comprising:
    contacting a region of the patient's skin with a transdermal delivery device with an antigen composition applied to or impregnated on the transdermal delivery device, wherein the antigen composition comprises 50 to 100 μg of MPB64,
    removing the transdermal delivery device after one to seven days, and
    examining the region of the patient's skin for an immune response in the form of erythema, induration, or the appearance of small red vesicles, wherein the detection of an immune response on the skin indicates the patient has an active tuberculosis infection.

2. The method of claim 1, wherein the antigen composition further comprises a surfactant.

3. The method of claim 2, wherein the surfactant is a non-ionic surfactant.

4. The method of claim 3, wherein the surfactant is a polyoxyethylene sorbitan derivative.

5. The method of claim 4, wherein the polyoxyethylene sorbitan derivative is polyoxyethylene sorbitan monooleate.

6. The method of claim 1, wherein the transdermal device is medical tape, medical plaster, gauze, patch, adhesive solution, or a patch band.

* * * * *

UNITED STATES PATENT AND TRADEMARK OFFICE
CERTIFICATE OF CORRECTION

| | | |
|---|---|---|
| PATENT NO. | : 7,655,218 B2 | Page 1 of 1 |
| APPLICATION NO. | : 11/020974 | |
| DATED | : February 2, 2010 | |
| INVENTOR(S) | : Reiko M. Nakamura | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this

Twenty-third Day of November, 2010

David J. Kappos
*Director of the United States Patent and Trademark Office*